United States Patent [19]

Uchida et al.

[11] Patent Number: 4,871,700

[45] Date of Patent: Oct. 3, 1989

[54] REACTIVATING MO-BI-FE CATALYST USED IN PRODUCTION OF UNSATURATED ALDEHYDES

[75] Inventors: Shin-ichi Uchida, Himeji; Kozi Deguchi, Hyogo; Masamitsu Sasaki, Himeji, all of Japan

[73] Assignee: Nippon Shokubai Kagaku Kogyo Co., Ltd., Osaka, Japan

[21] Appl. No.: 193,065

[22] Filed: May 12, 1988

[51] Int. Cl.$^4$ .................. B01J 23/94; B01J 23/92; C07C 45/27; C07C 45/28

[52] U.S. Cl. .................................. 502/51; 502/52; 568/471; 568/479

[58] Field of Search .............. 502/51, 52, 38, 311

[56] References Cited

U.S. PATENT DOCUMENTS 3,882,159  5/1975  Callahan et al. .............. 260/465.3
4,052,333  10/1977  Lee .............................. 502/51
4,425,255  1/1984  Toyoda ......................... 502/38
4,604,370  8/1986  Sarumaru et al. .............. 502/38
4,732,884  3/1988  Sarumaru et al. .............. 502/311

*Primary Examiner*—Paul E. Konopka
*Attorney, Agent, or Firm*—Sherman and Shalloway

[57] ABSTRACT

A method of reactivating a catalyst having reduced activity as a result of having been used in producing an unsaturated aldehyde as a main product by catalytic vapor-phase oxidation reaction of propylene, isobutylene or tertiary butanol, said catalyst being a catalytic oxide comprising molybdenum, bismuth and iron with a Mo:Fe atomic ratio of 12:at least 0.1. The method comprises heat-treating the used catalyst at a temperature of 300° to 500° C. in the presence of a flowing oxidizing gas containing at least 5% by volume of molecular oxygen and at least 0.1% by volume of steam.

16 Claims, No Drawings

REACTIVATING MO-BI-FE CATALYST USED IN PRODUCTION OF UNSATURATED ALDEHYDES

This invention relates to a method of regenerating and activating a catalyst. Specifically, it relates to a method of regenerating and activating a catalyst for production of unsaturated aldehydes comprising molybdenum, bismuth and iron. More specifically, it relates to an advantageous method of regenerating and activating the aforesaid catalyst having reduced activity as a result of having been used for a long period of time in a fixed bed reactor.

Multi-component catalytic oxides comprising molybdenum, bismuth and iron have widely been used for the production of acrolein from propylene and methacrolein from isobutylene or tertiary butanol (see, for example, Japanese Patent Publications Nos. 42241/1972, 42242/1972, 27490/1972, 45256/1980, 61011/1982, 23370/1983 and 49535/1983, and Japanese Laid-Open Patent Publications Nos. 73488/1978 and 31727/1984). When they are used for a long period of time, their activity is gradually reduced. It is also known that the reduction of their activity is accelerated when for enhanced productivity, the concentration or the space velocity of the starting gas is increased and consequently loads on the catalysts are increased. It is known that the main cause of the reduced activity of the catalysts in such a case is the scattering of molybdenum contained in the catalysts. Accordingly, many of the previously proposed methods for regenerating and activating such catalysts involve supplementing them with molybdenum.

For example, U.S. Pat. No. 3,882,159 discloses a method of reactivating a catalyst having degraded activity as a result of having been used in the ammoxidation reaction of propylene, which comprises bringing the degraded catalyst into contact with flowable particles of an inert carrier containing molybdenum in a fluidized bed reactor at a temperature of 200° to 600° C.

U.S. Pat. No. 4,425,255 proposes a method of reactivating a catalyst degraded as a result of having been used in the production of acrolein by oxidizing propylene, which comprises treating the degraded catalyst with a reducing gas containing hydrogen or a lower hydrocarbon at a temperature of 200° to 700° C., and then heat-treating it with a molecular oxygen-containing gas, i.e. an oxidizing gas, at a temperature of 500° to 700° C.

These prior methods, however, are troublesome because a substance for catalyst reactivation has to be newly prepared, or two gases, i.e. the reducing and oxidizing gases, should be prepared and the heat-treatment is necessary.

U.S. Pat. No. 4,604,370 proposes a method of regenerating a multi-component molybdenum-bismuth type oxide catalyst degraded as a result of having been used in producing acrolein or methacrolein by oxidizing propylene or isobutene, which comprises heat-treating the degraded catalyst in an atmostphere substantially composed of air at a temperature of 380° to 540° C. This method is based on the finding that the catalyst used in the above oxidation reaction is degraded in activity because at the start of the reaction, molybdenum is localized on the surface of the catalyst particles, and as the reaction proceeds, the molybdenum scatters. When by this method, the degraded catalyst is contacted with air for about 10 days at a temperature of as high as more than 380° C., especially more than 400° C., molybdenum diffuses within the particles and is supplied to the surface of the catalyst particles. It is never advantageous, however, to expose the catalyst to such an oxidizing atmosphere at high temperatures for a long period of time. Even if the catalyst activity is restored, the extent of its restoration cannot but be small.

It is an object of this invention to provide a method which can reactivate such multi-component molybdenum-bismuth oxide catalysts at lower temperatures.

The present inventors made investigations in order to achieve this object, and have found that such degraded catalysts can be reactivated and regenerated advantageously at lower temperatures within a shorter period of time by including oxygen in an amount above a certain limit and a small amount of steam into a hot gas for treating the catalysts.

According to this invention, there is provided a method of reactivating a catalyst having reduced activity as a result of having been used in producing an unsaturated aldehyde as a main product by catalytic vapor-phase oxidation reaction of propylene, isobutylene or tertiary butanol, said catalyst being a catalytic oxide comprising molybdenum, bismuth and iron with a Mo:Fe atomic ratio of 12:at least 0.1, preferably 12:0.5–10; which comprises heat-treating the used catalyst at a temperature of 300° to 500° C., preferably 300° to 380° C., in the presence of a flowing oxidizing gas containing at least 5% by volume, preferably 10 to 20% by volume, of molecular oxygen and at least 0.1% by volume, preferably 0.2 to 20% by volume, of steam.

The multi-component Mo-Bi-Fe type oxide catalysts to which the present invention is applied are used to produce acrolein or methacrolein as a main product by the catalytic vapor-phase oxidation reaction of propylene, isobutylene or tertiary butanol. In the catalysts, the atomic ratio of Mo to Fe is 12: at least 0.1, preferably 12:0.5–10. It is known that such catalyst systems, after having been used for a long period of time, are reduced in activity (conversion of the starting compound) to a greater extent than in selectivity for the useful desired product.

Investigations of the present inventors have shown that the cause of the reduction of activity (degradation of the catalyst performance) is not the scattering of the molybdenum component (such as $MoO_3$) mentioned hereinabove. Certainly, the present inventors know from experience that in a certain catalyst system, the presence of $MoO_3$ is observed before it is used, and after use for a long period of time, the content of $MoO_3$ in the catalyst decreases as a whole and increases on the lower-temperature side (outlet side) of the catalyst layer filled in the reactor; and this seemingly suggests relationship between catalyst degradation and the amount of Mo in the catalyst in a long-term reaction. However, the present inventors have also acertained that even when Mo is prevented, to the greatest possible extent, from existing in the catalyst as an oxide of Mo alone (for example, when Mo is coordinated to a saturated condition with another additive element such as Fe, Co, Ni or Bi), the catalyst performance can be maintained excellent.

It is said that as much literature shows, components which generally contribute to catalyst activity are, for example, bismuth molybdenum and molybdenum trioxide. Japanese Patent Publication No. 28180/1981 proposes an oxide catalyst having the composition $Co_{8-10}Mo_{12}Bi_{0.5-2}Fe_{0.5-2}O_x$ (x: a number which satisfies the atomic ratio) for the production of an α,β-unsaturated aldehyde by oxidizing an olefin, in which the active phase contains a crystalline phase represented by $Bi_2Fe_2Mo_2O_{12}$. This patent document discloses that the active phase simultaneously contains crystalline phases $Bi_2Mo_2Fe_2O_{12}$, $CoMo_4$, $Bi_2(MoO_4)_3$, and $Fe_2(MoO_4)_3$. The present inventors examined changes in various physical properties of catalysts such as the specific surface area, pore volume and acidity, and compared unused catalysts with catalysts having reduced activity in respect of physical and chemical differences by utilizing X-ray diffractometry, etc. These investigations have led to the discovery that the change in the amount of acid by the n-butylamine method and the formation of iron molybdate which is a compound of trivalent iron and Mo and an oxide composed of Mo, Fe and Bi have to do with the changes in catalyst performance which occur with the lapse of time. A specific example is shown below.

The surface areas (BET method) and pore volumes of a fresh catalyst having the composition $Co_6Fe_2Bi_2W_2Mo_{12}Rb_{0.5}$ (the atomic ratio excepting oxygen) and a catalyst of the same composition which had reduced performance (reduced conversion of isobutylene) as a result of having been used for 12000 hours in the catalytic vapor-phase reaction of isobutylene were measured. The former had a surface area of 3 m²/g and the latter had a surface area of 2.8 m²/g, showing no great difference. The pore volume of the former was 0.40 cc/g, and that of the later was 0.38 cc/g, showing no great difference. When the amount of acid was measured by the n-butylamine method on these catalysts, the former showed an acid amount of 20 micromoles/g, while the latter had an acid amount of 13 micromoles/g showing a drastic decrease. This showed that one cause of activity reduction has to do with the change of the amount of acid. This, in turn, suggested that by treating the catalyst with steam or the like at high temperature, restoration of the number of Bronsted acid sites would be able to be expected.

On the other hand, the present inventors examined changes in the crystalline phases by X-ray diffractometry, and confirmed that quite a contrary phenomenon to that described in the specification of the above-cited Japanese Patent Publication No. 28180/1981 occurred. Specifically, it was iron molybdate [$Fe_2(MoO_4)_3$] which mainly had to do with the active species crystalline phase. As the oxidation reaction of isobutene proceeded, iron molybdate reacted with bismuth molybdate to form $Bi_2Fe_2Mo_2O_{12}$ (or $Bi_3Fe_1Mo_2O_{12}$), and in proportion to the amount of this oxide formed, the activity of the catalyst was reduced and $Fe_2(MoO_4)_3$ decreased. Presumably, it was because this reaction proceeds particularly easily in a reducing atmosphere.

In the measurement of X-ray diffraction patttern (cathode Cu-Kα), the 2θ of the main peak was 29.2° for bismuth α-molybdate, 22.91° for iron molybdate, 30.7° for an oxide of bismuth, iron and molybdenum ($Fe_2Bi_2Mo_2O_{12}$ or $Bi_3Fe_1Mo_2O_{12}$), 12.6° for molybdenum trioxide and 26.4° for β-cobalt-molybdate. For example, when the peak height of β-cobalt-molybdate in the fresh catalyst in Example 1 given hereinafter is taken as 100, the peak heights of the above compounds are as shown below.

|  | Fresh catalyst | Catalyst used for 12,000 hrs. | Catalyst after treatment with oxygen and steam |
| --- | --- | --- | --- |
| α-bismuth molybdate | 40 | 40 | 39 |
| $Bi_2Fe_2Mo_2O_{12}$ | 0 | 15 | 3 |
| $Fe_2(MoO_4)_3$ | 8 | 1 | 8 |
| $MoO_3$ | 8 | 8 | 8 |
| β-$CoMoO_4$ | 100 | 101 | 99 |

When the catalyst having reduced activity as a result of such a long-term reaction was heat-treated at a high temperature in an atmosphere containing oxygen and steam, $Bi_2Fe_2Mo_2O_{12}$ decreased, and the peak of $Fe_2(MoO_4)_3$ revived.

The present inventors therefore worked on a method of reactivating a catalyst degraded as a result of having been used for a long period of time, and have found that by heat-treating the degraded catalyst in an oxidizing atmosphere free from hydrocarbon, namely in a gaseous atmosphere composed of at least 5% by volume of oxygen, at least 0.1% by volume of steam and the remainder being inert gases such as nitrogen and carbon dioxide gas at a temperature in the vicinity of 350° C. for several hours, $Bi_2Fe_2Mo_2O_{12}$ drastically decreases and the peak of $Fe_2(MoO_4)_3$ is revived, the amount of acid in the treated catalyst restored to the level of the acid amount of the fresh catalyst, and consequently, the original properties of the catalyst are revived and can be maintained again for a long period of time. This discovery has led to the accomplishment of the present invention.

It was found that only when the degrated catalyst has a Mo:Fe atomic ratio of 12:at least 0.1, especially 12:0.5–1.0, the catalyst can be regenerated at a relatively low temperature in the vicinity of 350° C. as in the present invention.

The reactivating method in accordance with this invention is effective on a catalyst used in a reaction slightly tending to involve reduction in which a gas containing a starting material in a high concentration (therefore the concentration of oxygen cannot be forcibly increased in view of the combustion range is used).

The effect of the treating method in accordance with this invention is sufficiently recognized at a temperature of 300° to 500° C. in an atmostphere containing at least 5% by volume of molecular oxygen and at least 0.1% by volume of steam. If the amount of the flowing gas corresponds to an apparent space velocity (SV) (the ratio between the amount of the gas and the amount of the catalyst) is at least 100 hr$^{-1}$, especially at least 500 hr$^{-1}$, the effect of the method appears with a treating time of about 5 hours. The effect, however, does not increase if the treatment is carried out for too long a time, for example more than 75 hours.

The degraded catalyst used in re-activation is preferably filled in a reactor as a fixed bed. A fluidized bed of the catalyst can also be effectively treated by the method of this invention.

According to the method of this invention, the degraded catalyst can be easily reactivated at a relatively low temperature of 300° to 500° C. using a gas containing at least 5% by volume of molecular oxygen and at least 0.1% by volume of steam at a space velocity of at least 100 hr$^{-1}$. There is no need to bring a special catalyst ingredient for activation into contact with the degraded catalyst, and the reactivation can be effected without taking the trouble of withdrawing the degraded catalyst from the reaction apparatus. The method of this invention, therefore, is very advantageous industrially.

The following examples further illustrate the method of this invention. It should be understood however that the method of this invention is not limited by these examples.

EXAMPLE 1

Cobalt nitrate [$Co(NO_3)_2.6H_2O$; 1260 g], 580 g of ferric sulfate [$Fe(NO_3)_3.9H_2O$], and 700 g of bismuth nitrate [$Bi(NO_3)_6.5H_2O$] were dissolved respectively in 800 ml of deionized water, 700 ml of deionizded water and 900 ml of deionized water containing 100 ml of concentrated nitric acid. Separately, 7,000 ml of deionized water was heated with agitation, and 1,529 g of ammonium molybdate [$(NH_4)_6Mo_2O_{24}.5H_2O$] and 377 g of ammonium para-tungstate [$(NH_4)_{10}W_{12}O_{41}.5H_2O$] were dissolved in it. To the resulting solution were added dropwise the above aqueous solutions of the three nitrates, and they were mixed. A solution of 53.2 g of rubidium nitrate ($RbNO_3$) in 200 ml of deionized water and then 325 g of 20% silica sol were successively added to the resulting mixed solution, and they were mixed. The suspension formed was evaporated to dryness while it was heated with stirring. After drying, the solid product was pulverized to obtain particles with a size of 3.0 to 5.0 mm. The paricles were calcined for 6 hours at 450° C. under an air current to prepare a catalytic oxide having the composition (atomic ratio of elements excepting oxygen) $Co_6Fe_2Bi_2W_2Mo_{12}Si_{1.5}Rb_{0.5}$.

1400 ml of the resulting catalyst was filled in a stainless steel reaction tube having an inside diameter of 25.0 mm and an outside diameter of 29.0 mm and equipped with a molten salt bath to a layer height of 2860 mm. The temperature of the salt bath was maintained at 330° C., and a starting gas composed of 6% by volume of isobutylene, 13.2% by volume of oxygen, 65.3% by volume of nitrogen, 15.0% by volume of steam and the remainder being isobutane, n-butane, propane, and inert gases such as carbon dioxide gas was introduced into the reaction tube at a space velocity of 1000 $hr^{-1}$ to perform oxidation of isobutylene (the normal oxidation reaction of isobutylene). As a result, the conversion of isobutylene was 99.5%; the selectivity for methacrolein was 77.0%; and the selectivity for methacrylic acid was 4.3%.

When this reaction was continuously carried out for 12,000 hours, the temperature of the salt bath rose to 340° C. The conversion of isobutylene became 90.6%; the selectivity for methacryloein became 76.8%; and the selectivity for methacrylic acid became 4.5%.

The reaction was then stopped. The temperature of the salt bath was increased to 375° C., and the supply of isobutylene in the starting gas was stopped. By using a gas comprising 2% by volume of steam, 19% by volume of oxygen and the remainder mainly consisting of nitrogen was used, and the catalyst was heat-treated for 10 hours. After this treatment, the temperature of the salt bath was lowered to 330° C., and in accordance with the above normal reaction, isobutylene was oxidized. The conversion of isobutylene was 99.6%; the selectivity for methacrolein was 76.9%; and the selectivity for methacrylic acid was 4.6%.

The changes in the properties of the catalyst were measured during the above period, and the results are shown in Table 1.

When this reaction was further continued for 8,000 hours, the temperature of the salt bath gradually rose to 340° C. But the conversion of isobutylene was 95.1%; the selectivity for methacrolein was 77.2%; and the selectivity for methacrylic acid was 4.0%.

EXAMPLE 2

8,000 ml of deionized water was heated with stirring, and 1,274 g of ammonium molybdate and 628 g of ammonium paratungstate were dissolved. Separately, 933 g of cobalt nitrate, 324 g of ferric nitrate and 389 g of bismuth nitrate were dissolved respectively in 600 ml of deionized water, 500 ml of deionized water and 500 ml of deionized water acidified by addition of 65 ml of concentrated nitric acid. These aqueous solutions of cobalt nitrate, ferric nitrate and bismuth nitrate were mixed, and the mixed solution was added dropwise to the aforesaid aqueous solution of ammonium molybdate and ammonium paratungstate. Subsequently, 325 g of 20% silica sol and a solution of 3.2 g of sodium hydroxide in 30 ml of deionized water were added. The resulting suspension was evaporated to dryness while it was heated with stirring. The solid product was molded and calcined at 450° C. for 6 hours under an air current to obtain a catalyst having the composition $Co_4Fe_1Bi_1W_3Mo_9Na_{0.1}Si_{1.35}$ (atomic ratio excepting oxygen).

The catalyst was filled in a reactor, and isobutylene was oxidized (the normal oxidation reaction) using a molten salt bath having a temperature of 340° C., by the method of Example 1. As a result, the conversion of isobutylene was 99.6%; the selectivity for methacrolein was 81.6%; and the selectivity for methacrylic acid was 3.5%. When this reaction was continued for 12,000 hours, the temperature of the salt bath rose to 350° C. The conversion of isobutylene was 89.2%; the selectivity for methacrolein was 81.4%; and the selectivity for methacrylic acid was 4.0%.

The reaction was then stopped, and the temperature of the salt bath was elevated to 370° C. Supply of isobutylene in the starting gas was stopped, and while passing a gas composed of 2.0% by volume of steam, 19% by volume of oxygen and the remainder consisting mainly of nitrogen through the catalyst layer, the catalyst was heat-treated for 10 hours. After the heat treatment, the temperature of the salt bath was lowered to 340° C., and the normal oxidation reaction of isobutylene was carried out in the same way as described above. As a result, the conversion of isobutylene was 99.5%; the selectivity for methacrolein was 81.4%; and the selectivity for methacrylic acid was 3.7%. The changes in the physical properties of the catalyst during this period were measured, and the results are shown in Table 1.

When this reaction was continued for 8,000 hours, the temperature of the salt bath gradually rose to 350° C. The conversion of isobutylene was 96.0%; the selectivity for methacrolein was 81.3%; and the selectivity for methacrylic acid was 3.9%.

EXAMPLE 3

In the heat-treatment of the catalyst after the oxidation reaction of isobutylene for 12,000 hours in Example 1, the steam content of the oxidizing gas was changed to 1, 10, 15 and 20% by volume. There was hardly any difference in the effect of the treatment as shown below.

When with a steam content was 1% by volume, the reaction after the heat-treatment was carried out at 330° C., the conversion of isobutylene was 99.6%, the selectivity for methacrolein was 77.1%, and the selectivity for methacrylic acid was 4.3%. When the reaction was further continued for 8,000 hours, the salt bath temperature rose to 340° C., but the result of the reaction was that the conversion of isobutylene was 96.2%, the selectivity for methacrolein was 77.0%, and the selectivity for methacrylic acid was 4.2%.

When with a steam content was 10% by volume, the reaction after the heat-treatment was carried out at 330° C., the conversion of isobutylene was 99.5%, the selectivity for methacrolein was 77.3%, and the selectivity for methacrylic acid was 4.2%. When the reaction was further continued for 8,000 hours, the salt bath temperature rose to 340° C., but the result of the reaction was that the conversion of isobutylene was 96.0%, the selectivity for methacrolein was 77.0%, and the selectivity for methacrylic acid was 4.1%.

When with a steam content was 15% by volume, the reaction immediately after the heat-treatment was carried out at 330° C., the conversion of isobutylene was 99.4%, the selectivity for methacrolein was 79.9%, and the selectivity for methacrylic acid was 4.5%. When the reaction was further continued for 8,000 hours, the salt bath temperature rose to 340° C., but the result of the reaction was that the conversion of isobutylene was 95.8%, the selectivity for methacrolein was 79.6%, and the selectivity for methacrylic acid was 4.4%.

When with a steam content was 20% by volume, the reaction immediately after the heat-treatment was carried out at 330° C., the conversion of isobutylene was 99.8%, the selectivity for methacrolein was 77.1%, and the selectivity for methacrylic acid was 4.5%. When the reaction was further continued for 8,000 hours, the salt bath temperature rose to 340° C., but the result of the reaction was that the conversion of isobutylene was 96.5%, the selectivity for methacrolein was 77.0%, and the selectivity for methacrylic acid was 4.2%.

EXAMPLE 4

The same reaction as in Example 1 as carried out for 12,000 hours, and the performance of the catalyst was measured. The result was that at a salt bath temperature of 340° C., the conversion of isobutylene was 90.1%, the selectivity for methacrolein was 76.9%, and the selectivity for methacrylic acid was 4.5%.

The reaction was then stopped, and the temperature of the salt bath was raised to 430° C. Isobutylene was removed from the reaction feed gas, and the gas was adjusted so that it was composed of 2% by volume of steam, 19% by volume of oxygen and the remainder consiting mainly of nitrogen. The adjusted gas was passed through the catalyst layer, and the catalyst was heat-treated for 5 hours.

After the heat-treatment, the temperature of the niter bath was lowered to 330° C., and again the normal oxidation reaction of isobutylene was carried out. The result was that the conversion of isobutylene was 99.0%, the selectivity for methacrolein was 77.1%, and the selectivity for methacrylic acid was 4.3%. When this reaction was continued further for 8,000 hours, the temperature of the salt bath became 340° C., and the result of the reaction was that the conversion of isobutylene was 94.6%, the selectivity for methacrolein was 77.3%, and the selectivity for methacrylic acid was 4.6%.

EXAMPLE 5

A catalyst having the composition $Co_6Fe_{0.3}Bi_2W_2Mo_{12}Si_{1.5}Rb_{0.5}$ (atomic ratio excepting oxygen) was prepared by the same procedure as in Example 1. 1400 ml of this catalyst was filled in a reactor, and the normal oxidation reaction of isobutylene was carried out at a salt bath temperature of 340° C., in the same way as in Example 1. The result was that the conversion of isobutylene was 99.2%, the selectivity for methacrolein was 75.1% and the selectivity for methacrylic acid was 2.9%.

After this reaction was continued for 12,000 hours, the temperature of the salt bath became 350° C. The conversion of isobutylene was 92.1%, the selectivity for methacrolein was 75.0%, and the selectivity for methacrylic acid was 3.0%. The reaction was stopped, and the temperature of the salt bath was raised to 375° C. Isobutylene was removed from the reaction feed gas, and the gas was adjusted so that it was composed of 2% by volume of steam, 19% by volume of oxygen and the remainder consisting mainly of nitrogen. The adjusted gas was passed through the catalyst layer, and the catalyst was heat-treated for 10 hours. Then, the temperature of the salt bath was returned to 340° C., and the normal oxidation reaction of isobutylene was carried out. The result was that the conversion of isobutylene was 97.2%, the selectivity for methacrolein was 75.3%, and the selectivity for methacrylic acid was 2.9%. After this reaction was further continued for 8,000 hours, the temperature of the salt bath reached 350° C., but the result was that the conversion of isobutylene was 96.4%, the selectivity for methacrolein was 75.1%, and the selectivity for methacrylic acid was 30%.

EXAMPLE 6

A catalyst having the composition $Co_4Fe_1Bi_1W_2Mo_{10}Si_{1.35}K_{0.06}$ (atomic ratio exceptingoxygen) was prepared by the same procedure as in Example 2.

1470 ml of the catalyst was filled in a stainless steel single tubular reactor having an inside diameter of 25.0 mm and an outside diameter of 29.0 mm and equipped with a salt bath to a layer height of 3000 mm. The temperature of the salt bath was maintained at 315° C., a starting gas composed of 10% by volume of propylene, 15% by volume of oxygen, 64.5% by volume of nitrogen, 10% by volume of steam and the remainder consisting of propane and inert gases such as carbon dioxide gas was introduced into the reactor at a space velocity of 1,300 hr$^{-1}$ (S.T.P.) to oxidize propylene (the normal oxidation reaction of propylene). The result was that the conversion of propylene was 97.2%, the selectivity for acrolein was 85.6% and the selectivity for acrylic acid was 7.2%.

After this reaction was continued for 16,000 hours, the temperture of the salt bath reached 325° C. and the result of the reaction was that the conversion of propylene was 93.1%, the selectivity for acrolein was 85.4%, and the selectivity for acrylic acid was 7.6%.

The reaction was then stopped, and the temperature of the salt bath was raised to 350° C. Propylene was removed from the reaction feed gas, and the gas was adjusted so that it was composed of 2% by volume of steam, 19% by volume of oxygen and the remainder consisting mainly of nitrogen. The adjusted gas was passed through the catalyst layer, and the catalyst was heat-treated for 5 hours. After the heat-treatment, the temperature of the salt bath was lowered to 315° C., and the normal oxidation reaction of propylene was carried out. The result was that the conversion of propylene was 97.3%, the selectivity for acrolein was 85.4%, and the selectivity for acrylic acid was 7.2%. After this reaction was further continued for 8,000 hours, the temperature of the salt became 325° C., but the result of the reaction was that the conversion of propylene was 96.1%, the selectivity for acrolein was 85.6%, and the selectivity for acrylic acid was 7.4%.

COMPARATIVE EXAMPLE 1

The same reaction as in Example 1 was carried out for 12,000 hours, the performance of the catalyst was measured. At a salt bath temperature of 340° C., the conversion of isobutylene was 91.0%, the selectivity for methacrolein was 76.9%, and the selectivity for methacrylic acid was 4.2%.

The reaction was stopped, and the temperature of the salt bath was lowered to 290° C. Isobutylene was removed from the reaction starting gas, and the gas was adjusted so that it was composed of 5% by volume of oxygen, 18.5% by volume of oxygen and and the remainder consisting mainly of nitrogen. By using the adjusted heat-treatment, the catalyst was heat-treated for 15 hours. After the heat-treatment, the temperature of the salt bath was returned to 330° C., and the normal oxidation reaction of isobutylene was carreid out. The result of the reaction was that the conversion of isobutylene was 88.5%, the selectivity of methacrolein was 77.0%, and the selectivity for methacrylic acid was 4.2%. This result shows that by heat-treatment at 290° C., the activity of the catalyst coult not be sufficiently restored.

COMPARATIVE EXAMPLE 2

The same reaction as in Example 1 was carried out for 12,000 hours, and the performance of the catalyst was measured. At a salt bath temperature of 340° C., the conversion of isobutylene was 90.4%, the selectivity for methacrolein was 77.0%, and the selectivity for methacrylic acid was 4.5%.

The reaction was then stopped, and the temperature of the salt bath was raised to 375° C. Isobutylene and steam were removed from the starting gas, and the catalyst was heat-treated for 10 hours using a gas containing molecular oxygen. After this heat-treatment, the temperature of the salt bath was returned to 330° C., and the normal oxidation reaction of isobutylene was carried out. As a result, the conversion of isobutylene was 93.6%, the selectivity for methacrolein was 77.2%, and the selectivity for methacrylic acid was 4.2%. This result shows that by heat-treatment in the absence of steam, the activity of the catalyst could not be sufficiently restored.

REFERENTIAL EXAMPLE

The changes in peak height in X-ray diffraction and the changes in the total amount of acids were measured on the catalysts prepared in the foreging Examples and Comparative Examples before using in the reactions, the catalysts after use in the continuous reactions for 12,000 or 16,000 hours, and the catalysts after the heat-treatments. The results are summarized in Table 1.

TABLE 1

Peak ratios by X-ray diffraction (the peak height of β-CoMoO₄ before use is taken as 100) and the total and amounts

| | Example 1 | | | Example 2 | | | Example 3 | | |
|---|---|---|---|---|---|---|---|---|---|
| | Before use | After use for 12,000 hours | After heat-treatment | Before use | After use for 12,000 hours | After heat-treatment | Before use | After use for 12,000 hours | After heat-treatment |
| α-bismuth molybdate | 40 | 40 | 39 | 40 | 39 | 40 | 40 | 40 | 40 |
| BiFeMoO compound | 0 | 15 | 3 | 0 | 13 | 2 | 0 | 13–15 | 1–3 |
| iron molybdate | 8 | 1 | 8 | 7 | 2 | 7 | 8 | 1 | 8 |
| molybdenum trioxide | 8 | 8 | 8 | 8 | 8 | 8 | 8 | 8 | 8 |
| β-cobalt molybdate | 100 | 101 | 99 | 100 | 101 | 100 | 100 | 100–101 | 99 |
| total acid amount (μmole/g) | 20 | 13 | 19 | 19 | 11 | 18 | 20 | 12–13 | 18–19 |

| | Example 4 | | | Example 5 | | | Example 6 | | |
|---|---|---|---|---|---|---|---|---|---|
| | Before use | After use for 12,000 hours | After heat-treatment | Before use | After use for 12,000 hours | After heat-treatment | Before use | After use for 12,000 hours | After heat-treatment |
| α-bismuth molybdate | 39 | 40 | 39 | 39 | 40 | 38 | 38 | 38 | 38 |
| BiFeMoO compound | 0 | 15 | 2 | 0 | 15 | 3 | 0 | 14 | 2 |
| iron molybdate | 9 | 1 | 9 | 8 | 1 | 7 | 9 | 1 | 9 |
| molybdenum trioxide | 8 | 8 | 8 | 8 | 8 | 8 | 8 | 8 | 8 |
| β-cobalt molybdate | 100 | 100 | 100 | 100 | 100 | 100 | 100 | 100 | 100 |
| total acid amount (μmole/g) | 21 | 13 | 20 | 19 | 13 | 20 | 25 | 15 | 24 |

| | Comp. Example 4 | | | Comp. Example 5 | | |
|---|---|---|---|---|---|---|
| | Before use | After use for 12,000 hours | After heat-treatment | Before use | After use for 12,000 hours | After heat-treatment |
| α-bismuth molybdate | 40 | 40 | 40 | 40 | 40 | 40 |
| BiFeMoO compound | 0 | 15 | 10 | 0 | 15 | 4 |
| iron molybdate | 8 | 1 | 3 | 8 | 1 | 7 |
| molybdenum trioxide | 8 | 8 | 8 | 8 | 8 | 8 |
| β-cobalt molybdate | 100 | 101 | 101 | 100 | 100 | 100 |
| total acid amount (μmole/g) | 20 | 13 | 19 | 20 | 13 | 14 |

What we claim is:

1. A method of reactivating a catalyst having reduced activity as a result of having been used in producing an unsaturated aldehyde as a main product by catalytic vapor-phase oxidation reaction of propylene, isobutylene or tertiary butanol, said catalyst being a catalytic oxide comprising molybdenum, bismuth and iron with a Mo:Fe atomic ratio of 12:at least 0.1; which method comprises heat-treating the used catalyst at a temperature of 300° to 380° C. in the presence of a flowing oxidizing gas containing at least 5% by volume of molecular oxygen and at least 0.1% by volume of steam.

2. The method of claim 1 wherein said Mo:Fe atomic ratio is 12:0.5–10.

3. The method of claim 1 wherein said flowing oxidizing gas contains 10 to 20% by volume of molecular oxygen.

4. The method of claim 1 wherein said flowing oxidizing gas contains 0.2 to 20% by volume of steam.

5. The method of claim 1 wherein said flowing oxidizing has an apparent space velocity of at least 100 $hr^{-1}$.

6. The method of claim 5 wherein said flowing oxidizing has an apparent space velocity of at least 500 $hr^{-1}$.

7. The method of claim 5 wherein said heat treatment is carried out for about 5 hours.

8. The method of claim 7 wherein said heat treatment is carried out for not more than 72 hours.

9. A method of reactivating a catalyst having reduced activity as a result of having been used in producing an unsaturated aldehyde as a main product by catalytic vapor-phase oxidation reaction of propylene, isobutylene or tertiary butanol, said catalyst being a catalytic oxide comprising molybdenum, bismuth and iron with a Mo:Fe atomic ratio of 12:0.1–10; which method comprises heat-treating the used catalyst at a temperature of 300° to 380° C. in the presence of a flowing oxidizing gas containing 5 to 20% by volume of molecular oxygen and 0.1 to 20% by volume of steam.

10. The method of claim 9 wherein said Mo:Fe atomic ratio is 12:0.5–10.

11. The method of claim 9 wherein said flowing oxidizing gas contains 10 to 20% by volume of molecular oxygen.

12. The method of claim 9 wherein said flowing oxidizing gas contains 0.2 to 20% by volume of steam.

13. The method of claim 9 wherein said flowing oxidizing gas has an apparent space velocity of at least 100 $hr^{-1}$.

14. The method of claim 13 wherein said flowing oxidizing gas has an apparent space velocity of at least 500 $hr^{-1}$.

15. The method of claim 13 wherein said heat treatment is carried out for about 5 hours.

16. The method of claim 15 wherein said heat treatment is carried out for not more than 72 hours.

* * * * *